(12) United States Patent
Lee

(10) Patent No.: US 6,872,532 B2
(45) Date of Patent: Mar. 29, 2005

(54) METHOD AND KIT FOR DETECTING WHITE SPOT SYNDROME VIRUS

(75) Inventor: Tzong Hae Lee, San Francisco, CA (US)

(73) Assignee: QGene Biotechnology, Inc., Kaohsiung (TW)

( * ) Notice: Subject to any disclaimer, the term of this patent is extended or adjusted under 35 U.S.C. 154(b) by 130 days.

(21) Appl. No.: 10/150,104

(22) Filed: May 20, 2002

(65) Prior Publication Data

US 2003/0215789 A1 Nov. 20, 2003

(51) Int. Cl.⁷ .......................... C12Q 1/68; C12P 19/34; C07H 21/02; C07H 21/04
(52) U.S. Cl. ........................ 435/6; 435/91.1; 435/91.2; 536/23.1; 536/24.33; 536/25.32; 536/26.6
(58) Field of Search ................... 435/6, 91.2; 536/22.1, 536/24.33, 25.32

(56) References Cited

U.S. PATENT DOCUMENTS

| | | | |
|---|---|---|---|
| 5,824,535 | A | 10/1998 | Kou et al. |
| 6,190,862 | B1 | 2/2001 | Kou et al. |

OTHER PUBLICATIONS

Arun K. Dhar et al., "Detection and Quantification of Infectious Hypodermal and Hematopoietic Necrosis Virus and White Spot Virus in Shrimp Using Real–Time Quantitative PCR and SYBR Green Chemistry", Journal of Clinical Microbiology, Aug. 2001, pp. 2835–2845.

Belcher CR et al., "Colourimetric PCR–based Detection of Monodon Baculovirus in Whole Penaeus Monodon Postlarvae", J. Virol. Methods, 1998 Sep.; 74(1):21–9 (Abstract Only).

Nunan LM et al., "Development of a Non–Radioactive Gene Probe by PCR for Detection on White Spot Syndrome Virus (WSSV)", J. Virol. Methods, Jan;63(1–2):193–201 (Abstract Only).

Hsu HC et al., "Studies on Effective PCR Screening Strategies for White Spot Syndrome Virus (WSSV) Detection in Penaeus Mondon Brooders", Dis. Aquat. Organ., 1999 Dec. 22;39(1):13–9.

Venegas CA et al., "Quasi–Immune Response of Penaeus Japonicus to Penaeid Rod–Shaped DNA Virus (PRDV)",0 Dis. Aquat. Organ., Aug. 31, 2000;42(2):83–9 (Abstract only).

Tang KF et al. "Detection and Quantification of Infectious Hypodermal and Hematopoietic Necrosis Virus in Penaeid Shrimp by Real–Time PCR", Dis. Aquat. Organ., Mar. 9;44(2):79–85 (Abstract Only).

Dhar AK et al., "Detection and Quantification of Infectious Hypodermal and Hematopoietic Necrosis Virus and White Spot Virus in Shrimp Using Real–Time Quantitative PCR and SYBR Green Chemistry", J. Clin. Microbiol., Aug. 2001;39(8):2835–45 (Abstract Only).

Abstract and Machine Translation of JP9201196 (published Aug. 5, 1997).

Primary Examiner—Kenneth R. Horlick
Assistant Examiner—Joyce Tung
(74) Attorney, Agent, or Firm—Stevens, Davis, Miller & Mosher, LLP

(57) ABSTRACT

A method for detecting white spot syndrome virus (WSSV) in a sample includes the steps of (a) adding to the sample a thermostable polymerase, appropriate nucleoside triphosphates, a nucleic-acid-binding fluorescent entity, and a pair of primers substantially complementary to a target nucleic acid having the sequence shown in SEQ ID NO: 1 or the complement of the target nucleic acid; (b) thermally cycling the sample between at least a denaturation temperature and an elongation temperature; (c) illuminating the sample with a selected wavelength of light that is absorbed by the fluorescent entity during the thermally cycling step; (d) determining the amount of fluorescence generated by the fluorescent entity; and (e) detecting the presence of the target nucleic acid by analyzing the amount of luminescence determined after at least one amplification cycle. The invention further provides kits for detection of WSSV in samples.

14 Claims, No Drawings

METHOD AND KIT FOR DETECTING WHITE SPOT SYNDROME VIRUS

BACKGROUND OF THE INVENTION

1. Field of the Invention

This invention relates to a method for detecting or quantifying white spot syndrome virus (WSSV) in a sample.

2. Description of the Related Art

In recent years, disease outbreaks have caused mass mortality among cultured shrimps (especially penaeid shrimp) in Taiwan and southeast Asia. Pathogens, such as bacteria, viruses, and fungi, along with environmental stressors such as temperature fluctuation, heavy rainfall, overfeeding, and industrial and agricultural-pollutants, are considered to be the major contributors for the outbreaks. Among these, viral infections are particularly of concern, primarily because viral diseases cannot be cured by therapeutic reagents and an early and sensitive detection of the disease is the most effective means for containment.

To date, nearly twenty penaeid shrimp viral diseases have been discovered. Among them, white spot syndrome virus (WSSV) is one of the major shrimp viruses due to its wide distribution and causes of high mortality in penaeid shrimp.

The recent discovery that exotic viruses remain infectious in frozen, commodity shrimp has led to serious concerns in the world. The best approach to manage any viral disease is to implement preventative measures to keep it out of the production system. These include disinfecting ponds and eliminating potential viral carriers prior to stocking, the use of fine screens at water inlets to remove potential carriers, avoidance of fresh feed (not heat processed) products that may contain crustacean species that are carriers or hosts for WSSV. Also, monitoring of all stocks through the use of polymerase chain reaction (PCR) for WSSV is an essential measure.

While the PCR technique as presently practiced is an extremely powerful method for amplifying nucleic acid sequences, the detection of the amplified material requires additional manipulation and subsequent handling of the PCR products to determine whether the target DNA is present.

Accordingly, there exists a need in the art for a rapid and sensitive method for detecting or quantifying WSSV in a sample.

SUMMARY OF THE INVENTION

It is an object of the present invention to develop a real-time PCR assay for directly detecting or quantifying white spot syndrome virus (WSSV) in a sample in which detection steps are minimized resulting in a method which may be performed quickly, accurately and easily with minimal operator skill.

The inventors have identified a sequence of WSSV DNA that is unique to this virus and not found in other related viral genomes. Using the sequence represented by SEQ ID NO:1, it has been possible to synthesize a variety of primers that hybridize to it. These can be used in developing a real-time PCR for the detection of WSSV in a sample.

One embodiment of the invention is directed to a method comprising: (a) adding to the sample a thermostable polymerase, appropriate nucleoside triphosphates, a nucleic-acid-binding fluorescent entity, and a pair of primers that have nucleotide sequences substantially complementary to a target nucleic acid having the sequence shown in SEQ ID NO:1 or the complement of the target nucleic acid; (b) thermally cycling the sample between at least a denaturation temperature and an elongation temperature, wherein the two primers in combination amplify the target nucleic acid represented by SEQ ID NO:1, or a section thereof; (c) illuminating the sample with a selected wavelength of light that is absorbed by the fluorescent entity during the thermally cycling step; (d) determining the amount of fluorescence generated by the fluorescent entity; and (e) detecting the presence of the target nucleic acid by analyzing the amount of luminescence determined after at least one amplification cycle. As the target sequence is unique to WSSV, this method can be used to detect WSSV in a sample, thus potentially providing information as to the likelihood of the sample donor suffering from the symptoms caused by the virus.

In another embodiment of the invention, a method for quantifying WSSV in a sample is provided. This method is based on the fact that the amount of fluorescence is related to the amount of the target nucleic acid in the sample. Specifically, this method involves (a) determining a threshold cycle number at which the amount of fluorescence generated by the fluorescent entity in a sample reaches a fixed threshold value above a baseline value; and (b) calculating the quantity of the target nucleic acid in the sample by comparing the threshold cycle number determined for the target nucleic acid in a sample with the threshold cycle number determined for target nucleic acid of known amounts in standard solutions.

In the methods of the present invention, nucleic-acid-binding fluorescent entity, e.g., a double strand specific nucleic acid binding dye or a fluorescently labeled oligonucleotide probe, is used for the detection and analysis of the amplified product without the need for any subsequent handling step, thereby allowing a high-through-put method for directly detecting and quantifying WSSV in a sample.

Preferably, after the aforementioned method is performed, the amount of fluorescence generated by the fluorescent entity is measured as a function of temperature to determine the melting profile of the amplified target nucleic acid or a section thereof. Thereafter, the amplified target nucleic acid or a section thereof can be characterized by analysis of the melting profile for confirmation of PCR specificity.

Preferred primers capable of hybridizing to the target sequence (SEQ ID NO:1) of the invention are the primers of SEQ ID NO:2 and SEQ ID NO:3.

The invention further provides kits for detection of WSSV in samples as described above. These kits comprise reagents suitable for performing methods as described above, and therefore for effecting detection, and preferably quantification, of WSSV in samples. A kit suitable for quantifying WSSV in a sample will comprise a target nucleic acid of SEQ ID NO:1 as described above; and one or more pairs of primers as described above that are suitable for amplifying the target nucleic acid sequence, or a section thereof. Preferred kits of the invention may also comprise one or more preferred primer pairs such as the primer pair represented by SEQ ID NO:2 and SEQ ID NO:3.

Other objects, advantages, and novel features of the invention will become more apparent from the following detailed description.

DETAILED DESCRIPTION OF THE PREFERRED EMBODIMENT

The present invention provides methods for detecting and quantifying the occurrence of white spot syndrome virus (WSSV) in samples. For example, methods of the invention may be used to detect and/or quantify the number of viral genomes present in a sample, quantitative methods being preferred. Methods according to the invention rely on amplifying a target nucleic acid by a real-time PCR method. The target sequence that is amplified in methods of the invention is the 131 base pair sequence of SEQ ID NO:1 or a section of it. Where the target sequence is a section of the sequence of SEQ ID NO:1, the section may be of any length provided that the section is unique to the WSSV genome. For example, a section may comprise up to 50, up to 100 or up to 130 of the nucleotides of SEQ ID NO:1. As the target sequence is unique to WSSV, methods of the invention can be used to detect and or quantify WSSV under a variety of circumstances. For example, it is desirable to detect and/or quantify WSSV in samples taken from cultured shrimps (especially penaeid shrimp) which may be infected with WSSV. Also, methods of the invention can be used to evaluate the effectiveness of antiviral drugs. In this case, cell cultures comprising WSSV can be assayed using methods of the invention, the resulting information being used to determine what concentration of antiviral agent to use.

According to one embodiment of the present invention, a high-through-put method for directly detecting WSSV in a sample is provided. First, the method of the present invention is performed by adding to the sample a thermostable polymerase, appropriate nucleoside triphosphates, a nucleic-acid-binding fluorescent entity, and a pair of primers capable of amplifying of the aforementioned target sequence to create an amplification medium.

It is preferred that the primers have nucleotide sequences substantially complementary to the target nucleic acid having the sequence shown in SEQ ID NO:1 or the complement of the target nucleic acid, in the sense that every nucleotide will base pair with the one with which it pairs most stably (A with T or U; C with G). However, small deviations from this rule may be allowed, so long as they do not prevent the primer from hybridizing with the target and control sequences and initiating amplification. Preferred primers capable of hybridizing to the target sequence (SEQ ID NO:1) of the invention are the primers of SEQ ID NO:2 and SEQ ID NO:3. Preferably, the primers of the invention will be in isolated form, for example in aqueous solution.

The term "nucleoside triphosphate" is used herein to refer to nucleosides present in either DNA or RNA and thus includes nucleosides which incorporate adenine, cytosine, guanine, thymine and uracil as base, the sugar moiety being deoxyribose or ribose.

Suitable nucleic-acid-binding fluorescent entity for detecting and monitoring DNA amplification include double strand specific nucleic acid binding dyes or fluorescently labeled oligonucleotide probes. Those skilled in the art will be familiar with the use of ethidium bromide in monitoring DNA amplification. When a double strand-specific fluorescent dye is present during amplification, fluorescence generally increases as more double stranded product is made. It is preferred that SYBR® Green I, which is well known in the art and available from Molecular Probes of Eugene, Oreg., be used as a double-strand-specific dye. The molecular structure of this dye is a trade secret, but it is recommended by the manufacturer as a more sensitive double-strand-specific dye for DNA detection. A suitable fluorescently labeled probe is an oligonucleotide with both a reporter fluorescent dye and a quencher dye attached. While the probe is intact, the proximity of the quencher greatly reduces the fluorescence emitted by the reporter dye by Förster resonance energy transfer (FRET) through space.

Thereafter, the amplification medium is placed in a thermocycler for performing a thermally cycling reaction between at least a denaturation temperature and an elongation temperature. Any number of amplification cycles that amplifies the target sequence to a sufficient degree may be used wherein 45 to 50 cycles is particularly preferred. The amplification medium is irradiated with a selected wavelength of light and the resulting fluorescence is detected using a CCD array to capture an image of all samples. Fluorescence values are recorded during every thermal cycle and represent the amount of product amplified to that point in the amplification reaction. Software built in the thermocycler collects the images throughout the thermal cycling of PCR and analyzes the data to generate an amplification plot for each sample by plotting fluorescence signal versus cycle number.

Finally, analysis of the products of the amplification reaction is then carried out. Quantitative analyses are preferred, though detection of the target nucleic acid sequence without quantification is also within the scope of the invention. Typically, the more template containing the target nucleic acid present at the beginning of the amplification reaction, the fewer number of cycles it takes to reach a point in which the fluorescent signal is first recorded as statistically significant above background. This point is defined as the $C_T$ (threshold cycle), and will always occur during the exponential phase of amplification. Since the amplified product of the target nucleic acid is only synthesized if the sample contains the target nucleic acid, the presence of the target nucleic acid can easily analyzed by determining if the calculated $C_T$ of a sample reaction is above a predetermined value. As the target sequence is unique to WSSV, the aforementioned method can be used to detect WSSV in a sample, thus potentially providing information as to the likelihood of the sample donor suffering from the symptoms caused by the virus.

In another embodiment of the invention, a method for quantifying WSSV in a sample is provided. In this embodiment, quantitation of target nucleic acid in unknown samples is accomplished by measuring $C_T$ and using a standard curve to determine the starting copy number. Specifically, this method involves (a) determining a $C_T$ at which the amount of fluorescence generated by the fluorescent entity in a sample reaches a fixed threshold value above a baseline value; and (b) calculating the quantity of the target nucleic acid in the sample by comparing the $C_T$ determined for the target nucleic acid in a sample with the $C_T$ determined for target nucleic acid of known amounts in standard solutions.

Preferably, DNA melting curves for different PCR products are acquired by fluorescence monitoring with double-strand-specific DNA specific dyes. Fluorescence data for melting curves is acquired by integrating the signal over 0.25–2.0 seconds during a linear temperature transition to 95° C. at 0.1–10° C./second. The fluorescence was continuously acquired and displayed at fluorescence versus temperature plots by software built in the thermocycler. As a PCR product is heated from the extension temperature to the denaturation temperature, any DNA in the sample is melted to single strands. This denaturation can be observed as a drop in the fluorescence of double-strand-specific DNA specific dye. Melting curve analysis can be used to differentiate intended product from nonspecific products such as primer dimers. Primer dimers melt over a wide range of low temperatures; very different from the sharp melting curves of specific PCR amplification products. Larger heterogeneous products have lower and broader melting curves when compared with pure PCR product. Therefore, the PCR products can be characterized by analysis of the melting profile thereof for confirmation of PCR specificity.

The invention also provides kits for detection of WSSV in samples as described above. These kits comprise reagents suitable for performing methods as described above, and therefore for effecting detection, and preferably quantification, of WSSV in samples. A kit suitable for quantifying WSSV in a sample will comprise a target nucleic acid of SEQ ID NO:1 as described above; and one or more pairs of primers as described above that are suitable for amplifying the target nucleic acid sequence, or a section thereof. Preferred kits of the invention may also comprise one or more preferred primer pairs such as the primer pair represented by SEQ ID NO:2 and SEQ ID NO:3. Typically, these will be provided in separate containers as they will be used in separate stages of a method according to the invention. Kits according to the invention may also comprise any other suitable reagents, for example, four different nucleoside triphosphates, a nucleic-acid-binding fluorescent entity or a thermostable polymerase.

The invention is more particularly described by way of examples, which should not be construed as limiting the invention thereto.

EXAMPLE 1
Real-Time Monitoring of PCR Amplification of WSSV

First, reaction mixture was prepared using concentrated stock solutions. The reaction mixture consisted of the following:

| Reagents | Final Conc. |
|---|---|
| PCR buffer | 1x |
| Thermostable Polymerase | 0.7 unit |
| dNTPs | 100 mM each |
| WSSV5 (SEQ ID NO:2) | 0.5 $\mu$M |
| WSSV6a (SEQ ID NO:3) | 0.5 $\mu$M |
| SYBR ® Green I | 3.75x |

Then, ten microliters of the reaction mixture was aliquoted per reaction tube and 5 $\mu$l of sample (total DNA isolated from various tissues of normal and WSSV-infected shrimp) was added. In addition, 10 $\mu$l mineral oil per individual tube was added. It is preferred that WSSV Optimal Buffer™ which contains water, tris, triston, MgCl, KCl and BSA, and is available from QGENE Biotechnology Inc. be used as a PCR buffer. In addition, thermal stable DNA polymerases which activate upon heating to high temperatures (e.g., above 60° C.) may be used. Suitable thermal stable DNA polymerases include the ones described in Roche U.S. Pat. No. 5,677,152. Cycling was performed in GeneAmp® 5700 Sequence Detection 20 System and the following cycling conditions were used:

| 95° C.: | 10 min | (1x) |
|---|---|---|
| 95° C.: | 30 sec | (50x) |
| 60° C.: | 30 sec | (50x) |
| 72° C.: | 45 sec | (50x) |

The $C_T$ value is 50 when using specific-pathogen-free (SPF) shrimp DNA as a negative control. The $C_T$ values were less than 40 when virus infected samples were used as templates.

EXAMPLE 2
Quantitative Measurements Using Real-Time Monitoring of WSSV

Ten microliters of the aforementioned reaction mixture was aliquoted per reaction tube and 5 $\mu$l of standard (different dilutions of a stock ($1 \times 10^8$ copies/$\mu$l) containing the target nucleic acid of SEQ ID NO:1) was added. In addition, 10 $\mu$l mineral oil per individual tube was added. Thereafter, a standard curve is generated by plotting the $C_T$ values, with 95% confidence intervals, against the logarithm of the initial copy numbers. Accordingly, quantitation of the amount of target nucleic acid in unknown samples is accomplished by measuring $C_T$ and using the standard curve to determine the starting copy number.

Although the invention has been explained in relation to its preferred embodiment, it is to be understood that many other possible modifications and variations can be made without departing from the spirit and scope of the invention as hereinafter claimed.

What is claimed is:

1. A method for detecting white spot syndrome virus in a sample, the method comprising:
adding to the sample a thermostable polymerase, appropriate nucleoside triphosphates, a nucleic-acid-binding fluorescent entity, and a pair of primers that have nucleotide sequences substantially complementary to a target nucleic acid having the sequence shown in SEQ ID NO:1 or the complement of the target nucleic acid;
thermally cycling the sample between at least a denaturation temperature and an elongation temperature, wherein the two primers in combination amplify the target nucleic acid represented by SEQ ID NO:1, or a section thereof;
illuminating the sample with a selected wavelength of light that is absorbed by the fluorescent entity during the thermally cycling step;
determining the amount of fluorescence generated by the fluorescent entity; and
detecting the presence of the target nucleic acid by analyzing the amount of luminescence determined after at least one amplification cycle.

2. The method as claimed in claim 1, wherein one primer is the nucleic acid molecule of SEQ ID NO:2 and the other primer is the nucleic acid molecule of SEQ ID NO:3.

3. The method as claimed in claim 1, wherein the method is used to determine the quantity of the target nucleic acid in a sample, the method further comprises:
determining a threshold cycle number at which the amount of fluorescence generated by the fluorescent entity in a sample reaches a fixed threshold value above a baseline value; and
calculating the quantity of the target nucleic acid in the sample by comparing the threshold cycle number determined for the target nucleic acid in a sample with the threshold cycle number determined for target nucleic acid of known amounts in standard solutions.

4. The method as claimed in claim 3, wherein one primer is the nucleic acid molecule of SEQ ID NO:2 and the other primer is the nucleic acid molecule of SEQ ID NO:3.

5. The method as claimed in claim 1, wherein the fluorescent entity comprises a double strand specific nucleic acid binding dye.

6. The method as claimed in claim 5, further comprising the step of:
measuring the amount of fluorescence as a function of temperature to determine the melting profile of the amplified target nucleic acid or a section thereof; and
characterizing the amplified target sequence or a section thereof by analysis of the melting profile.

7. The method as claimed in claim 6, wherein one primer is the nucleic acid molecule of SEQ ID NO:2 and the other primer is the nucleic acid molecule of SEQ ID NO:3.

8. The method as claimed in claim 1, wherein the fluorescent entity comprises a fluorescently labeled oligonucleotide probe that hybridizes to the target nucleic acid or the complement of the target nucleic acid.

9. A kit for detection of white spot syndrome virus in a sample, the kit comprising:
a nucleic acid consisting of the sequence shown in SEQ ID NO:1; and
a pair of primers that have nucleotide sequences substantially complementary to the nucleic acid or the complement of the nucleic acid.

10. The kit as claimed in claim 9, further comprising:
four different nucleoside triphosphates;
a nucleic-acid-binding fluorescent entity; and
a thermostable polymerase.

11. The kit as claimed in claim 9, wherein the fluorescent entity comprises a double strand specific nucleic acid binding dye.

12. The kit as claimed in claim 9, wherein the fluorescent entity comprises a fluorescently labeled oligonucleotide probe that hybridizes to an isolated nucleic acid or the complement of the isolated nucleic acid.

13. The kit as claimed in claim 9, wherein one primer is the nucleic acid molecule of SEQ ID NO:2 and the other primer is the nucleic acid molecule of SEQ ID NO:3.

14. A nucleic acid molecule selected from the group consisting of:

5' GAG ATT GAG TTT GAG AGA TGC 3' and (SEQ ID NO:2)

5' CCT GGA TCT GTT GTT GAT CC 3'. (SEQ ID NO:3)

* * * * *

SEQUENCE LISTING

<160> NUMBER OF SEQ ID NOS: 3

<210> SEQ ID NO 1
<211> LENGTH: 131
<212> TYPE: DNA
<213> ORGANISM: white spot syndrome baculovirus

<400> SEQUENCE: 1

```
gagattgagt ttgagagatg cataattcta gtagaggatt ttaatagtgg aactattact      60
tcaaacacta tgcagtacag gtccaacgct tacaaaatca gagtagtaga aggatcaaca     120
acagatccag g                                                          131
```

<210> SEQ ID NO 2
<211> LENGTH: 21
<212> TYPE: DNA
<213> ORGANISM: white spot syndrome baculovirus -continued

```
<400> SEQUENCE: 2
gagattgagt ttgagagatg c                                                    21

<210> SEQ ID NO 3
<211> LENGTH: 20
<212> TYPE: DNA
<213> ORGANISM: white spot syndrome baculovirus

<400> SEQUENCE: 3
cctggatctg ttgttgatcc                                                      20
```